United States Patent [19]

Sugiyama et al.

[11] Patent Number: 4,579,747

[45] Date of Patent: Apr. 1, 1986

[54] DIPEPTIDE CRYSTALS, AND PROCESS FOR THEIR PRODUCTION

[75] Inventors: Katsumi Sugiyama, Kawasaki; Toshiyuki Ozawa, Ninomiya; Nobuya Nagashima, Tokyo; Yoshinobu Uchida, Yokosuka, all of Japan

[73] Assignee: Ajinomoto Company, Incorporated, Tokyo, Japan

[21] Appl. No.: 589,005

[22] Filed: Mar. 13, 1984

[51] Int. Cl.$^4$ ............................................. A23L 1/236
[52] U.S. Cl. .................................... 426/548; 426/465
[58] Field of Search ............... 426/548, 648, 443, 465; 260/707

[56] References Cited

U.S. PATENT DOCUMENTS

| | | | |
|---|---|---|---|
| 4,465,694 | 8/1984 | Okada | 426/548 |
| 4,486,455 | 12/1984 | Wolf et al. | 426/548 |
| 4,495,213 | 1/1985 | Wolf et al. | 426/548 |

FOREIGN PATENT DOCUMENTS 954741  9/1974  Canada ............................... 426/545

OTHER PUBLICATIONS

Glicksman et al., 1975, Patent Specification 59,258/73.

*Primary Examiner*—Raymond Jones
*Assistant Examiner*—Carolyn Paden
*Attorney, Agent, or Firm*—Oblon, Fisher, Spivak, McClelland & Maier

[57] ABSTRACT

$\alpha$-L-aspartyl-L-phenylalanine methyl ester II type crystals consisting of two types of crystals, $II_A$ and $II_B$ type, which interconvert from one to the other depending upon the equilibrium moisture content of the crystals, wherein one type of crystal, $II_a$, exhibits X-ray diffraction peaks at angles of diffraction of at least 20.6°, 21.2°, 5.0° and 11.1°, and the other type of crystal, $II_B$, exhibits X-ray diffraction peaks at angles of diffraction of at least 15.2°, 11.1°, 19.6° and 4.5°, as measured by X-ray diffractometer using $CuK_\alpha$ radiation and wherein the equilibrium moisture content of either of the crystals at a relative humidity of 78% is not higher than about 3%.

6 Claims, 5 Drawing Figures

DIPEPTIDE CRYSTALS, AND PROCESS FOR THEIR PRODUCTION

BACKGROUND OF THE INVENTION

1. Field of the Invention

This invention relates to dipeptide crystals having a sweet flavor, as well as to a process for their production. The present invention also relates to tablets containing the sweet dipeptide crystals which have excellent storage stability, and also to a process for the production thereof.

2. Description of the Prior Art

α-L-Aspartyl-L-phenylalanine methyl ester (hereinafter referred to as AP), known popularly as Aspartame, is a low calorie sweetener having a sweetening quality similar to sucrose which is pleasant. AP has attracted considerable attention lately in this regard. However, when the practical use of this substance is considered as a sweetener, several properties of AP such as low solubility and dispersibility present serious disadvantages.

Further, AP is relatively unstable to heat and when it is heated it is easily converted into a diketopiperadine and loses sweetness. For example, when a solution of AP is heated to 80° C. for about 5 hours, approximately 20% of the AP is decomposed. Hence, even in the production of AP, the production steps must be monitored so as not to exceed 60° C.

To date, two types of AP crystals have been known to exist. These crystals are generally known as I type crystals and more specifically as $I_A$ or $I_B$ type crystals. Both varieties of I type crystals are very hygroscopic resulting in coloration and decomposition during storage. Additionally, the pelletizability and fluidizability of powders containing these I type crystals is very poor.

The hygroscopic nature of these crystals also present problems when attempting to formulate a usable AP tablet. For example, in the case of effervescent tablets, either moisture absorbed or generated internally by chemically reaction of the effervescing agents (basic) and neutralizing agents (acidic) can cause adhesion between the individual tablets or between the tablets and the container. Further, the reaction of effervescing and neutralizing agents reduces tablet effervescence during storage and hence, the available tablet effervescence upon use is diminished. Due to the reduction in effervescence, the solubility of the tablet is greatly reduced.

Thus, a need clearly continues to exist for crystals of AP having excellent storage stability and which are very stable even in the presence of excipients, effervescing agents or neutralizing agents. Further, a need continues to exist for AP tablets which exhibit a reduced rate of neutralization reaction thus maintaining tablet effervescence and high tablet solubility.

SUMMARY OF THE INVENTION

Accordingly, it is an object of the present invention to provide AP crystals which have excellent storage stability and which are stable even in the presence of excipients, effervescing agents or neutralizing agents.

It is also an object of this invention to provide a process for producing such AP crystals.

Moreover, it is an object of the present invention to provide AP tablets which exhibit a reduced rate of neutralization reaction to maintain tablet effervescence and high tablet solubility.

Further, it is also an object of this invention to provide a process for producing such tablets.

According to the present invention, the foregoing and other objects are attained by providing α-L-aspartyl-L-phenylalanine methyl ester II type crystals, $II_A$ and $II_B$ type which interconvert from one to the other depending upon the equilibrium moisture content of the crystals, wherein one type of crystal ($II_A$ type) exhibits X-ray diffraction peaks at angles of diffraction of at least 20.6°, 21.2°, 5.0° and 11.1°, and the other type of crystal ($II_B$ type) exhibits X-ray diffraction peaks at angles of diffraction of at least 15.2°, 11.1°, 19.6° and 4.5°, as measured by an X-ray diffractometer using $CuK_\alpha$ radiation and wherein the equilibrium moisture content of either of the crystals at a relative humidity of 78% is not higher than 3%.

BRIEF DESCRIPTION OF THE DRAWINGS

FIGS. 1-4 are X-ray diffraction patterns measured by a powder X-ray diffractometer, in which FIG. 1 is for $II_A$ type crystals, FIG. 2 is for $II_B$ type crystals, FIG. 3 is for $I_A$ type crystals and FIG. 4 is for $I_B$ type crystals.

DETAILED DESCRIPTION OF THE PREFERRED EMBODIMENTS

According to the present invention, it has been surprisingly discovered that by drying the conventional I type crystals, i.e., $I_A$ or $I_B$ type crystals, at about 80° C. or higher, either individually or together as a mixture, two new types of crystals are obtained, which are themselves interconverting according to the humidity. These new crystal types, $II_A$ and $II_B$ type, absorb very little moisture and are easily pelletizable and have good fluidizability. These crystals have excellent storage stability and surprisingly it has been found that even when I type crystals are dried at 80° C., the amount of AP decomposed on the production of these new crystals is extremely low.

Accordingly, the present invention relates to AP II type crystals which consist of two kinds of crystals, $II_A$ type and $II_B$ type, which interconvert from one type to the other according to the moisture content.

The $II_A$ type crystals show peaks of diffracted X-rays at angles of diffraction of at least 20.6°, 21.2°, 5.0° and 11.1°. The $II_B$ type crystals show peaks of diffracted X-rays at angles of diffraction of at least 15.2°, 11.1°, 19.6° and 4.5° as measured by an X-ray diffractometer using $CuK_\alpha$ radiation. Moreover, the equilibrium moisture content of either of the crystals at a relative humidity of 78% is not higher than about 3%.

The II type crystals of AP can be described in terms of physical properties.

(1) X-ray Diffraction

Figure 1:
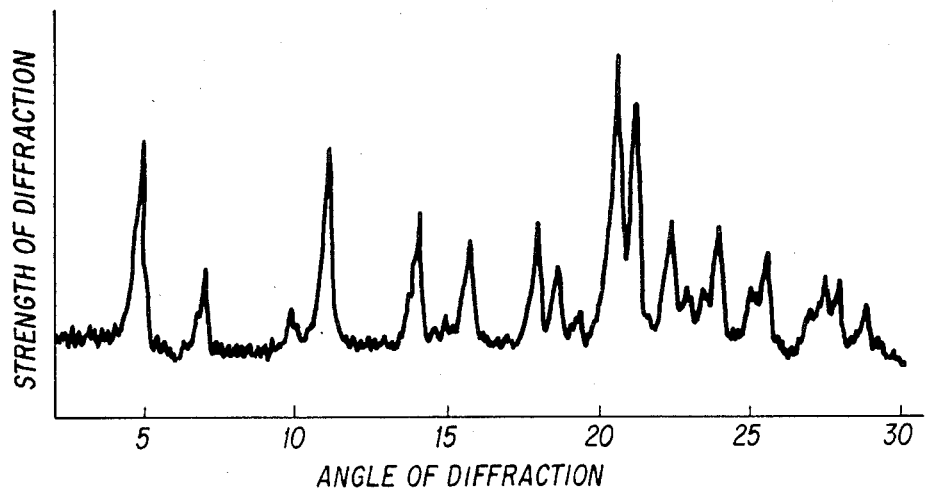
Figure 2:
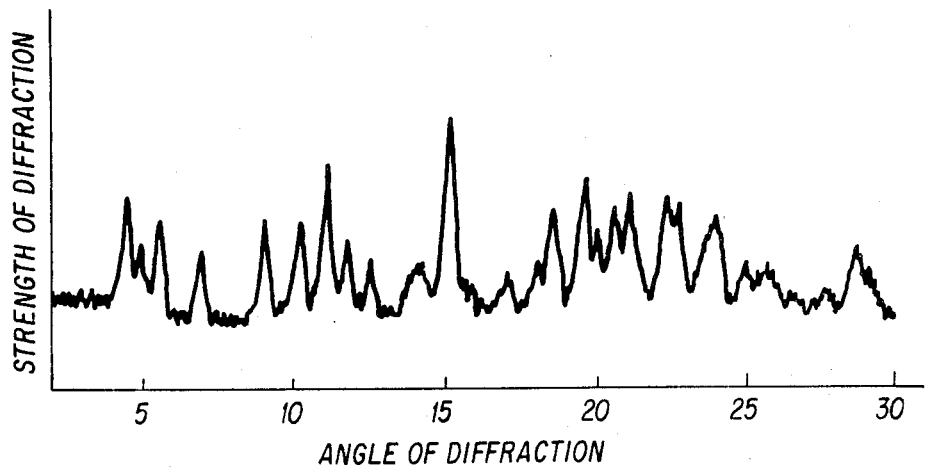
Figure 3:
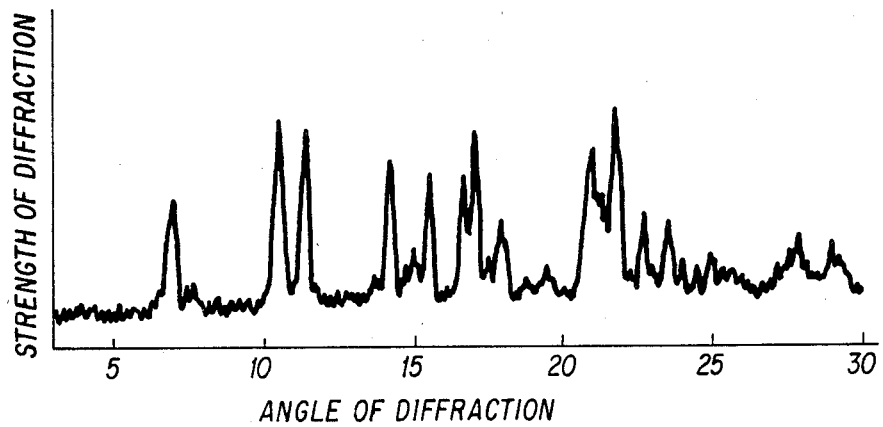
Figure 4:
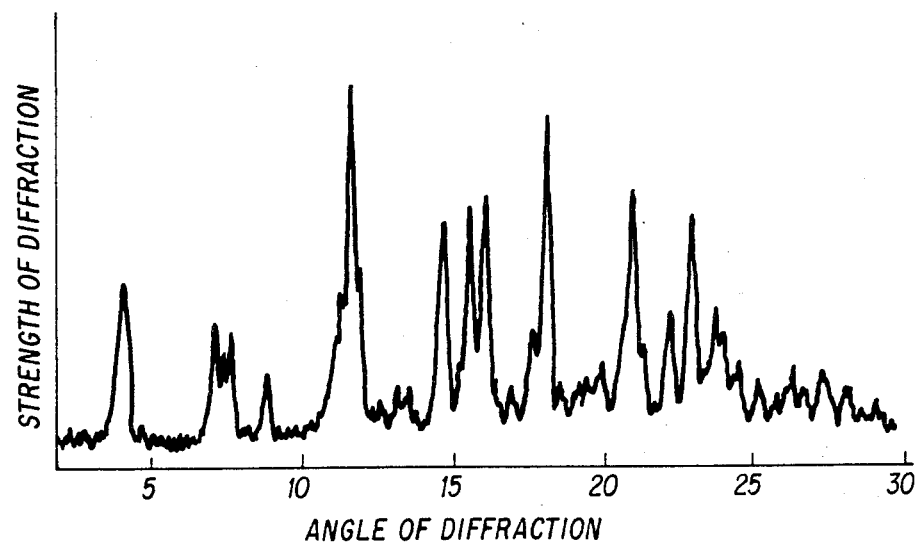
Figure 5:
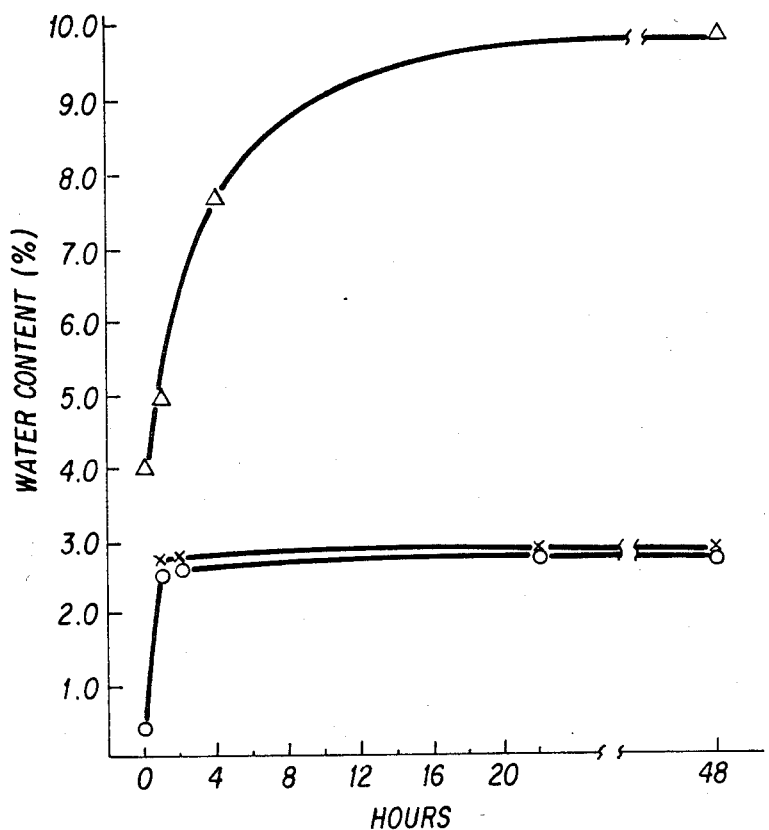
FIG. 5 illustrates the results of the measurement of the moisture absorption characteristics of the various crystals. The mark "o" corresponds to $II_B$ type crystals, mark "x" to $II_A$ type crystals and mark "Δ" to $I_B$ type crystals.

An X-ray diffraction pattern of $II_A$ type crystals in the region $2\theta = 3-30°$ with a powder X-ray diffractometer using $CuK_\alpha$ radiation is shown in FIG. 1; and X-ray diffraction pattern of $II_B$ type crystals in FIG. 2; and X-ray diffraction pattern of the conventional $I_A$ type crystals in FIG. 3; and an X-ray diffraction pattern of $I_B$ type crystals in FIG. 4.

As is clear from the figures, the peaks appearing at angles of diffraction of 20.6°, 21.2°, 5.0° and 11.1° in $II_A$ type crystals and the peaks appearing at angles of diffraction of 15.2°, 11.1°, 19.6° and 4.5° in $II_B$ type crystals are found in neither conventional $I_A$ type crystals nor $I_B$ type crystals, and therefore $II_A$ type crystals and $II_B$ type crystals can be distinguished from I type crystals by these diffracted peaks.

(2) Melting Point $II_A$ type crystals 163° C. (dec.)
$II_B$ type crystals 171° C. (dec.)
$I_B$ type crystals 172° C. (dec.)

(3) Degree of Optical Rotation $II_A$ type crystals $[\alpha]_D^{20} = 15.9$
$II_B$ type crystals $[\alpha]_D^{20} = 16.1$
$I_B$ type crystals $[\alpha]_D^{20} = 16.0$ (4) Moisture Content It is about 0.9% to about 3% with $II_A$ type crystals and about 0.9% or less with $II_B$ type crystals, and within this range it changes continuously according to the humidity. On the other hand, it is about 6% or higher with $I_A$ type crystals and about 2% to about 6% with $I_B$ type crystals, and within this range it changes continuously according to the humidity. Wet crystals obtained by conventional crystallization are of $I_A$ type.

(5) Moisture Absorption 50 g of each of the various AP crystals is spread on a tray and left in a constant temperature constant humidity cell kept at a temperature of 34° C. and a relative humidity of 78% to measure the change in moisture content with time, the results of which are shown in Table 5. In the figure, mark "o" stands for the case where $II_B$ type crystals were used at the start of measurement, mark "x" for $II_A$ type crystals and mark "Δ" for $I_B$ type crystals.

(6) Crystal Transition

The respective crystals 48 hours after the moisture absorption test in the previous section were measured by a powder X-ray diffractometer to find that they had changed into the crystals shown in the following table.

| Start of Measurement (Moisture) | 48 Hours Later (Moisture) |
|---|---|
| $I_B$ type (4.1%) | $I_A$ type (9.8%) |
| $II_A$ type (2.7%) | $II_A$ type (2.9%) |
| $II_B$ type (0.4%) | $II_B$ type (2.8%) |

(7) Storage Stability 0.7–1.2 g portions of the respective AP crystals are sealed into 100 ml glass ampules, stored in constant temperature cells at 55° C. and 80° C. respectively, and the percent of AP remaining is measured by an amino acid analyzer in each case. The results are shown in the following table.

| AP Crystals | | Percent of AP Remaining (%) | | |
|---|---|---|---|---|
| Crystal Form | Moisture | 0 Day | 45 Days | 75 Days |
| STORED AT 55° C. | | | | |
| $I_B$ type | 4.2% | 100% | 94% | 72% |
| $II_B$ type | 0.4 | 100 | 99 | 100 |
| $II_A$ type | 2.9 | 100 | 100 | 100 |
| STORED AT 80° C. | | | | |
| $I_B$ type | 4.1% | 100% | 74% | 40% |
| $II_B$ type | 0.4 | 100 | 100 | 100 |
| $II_A$ type | 2.7 | 100 | 99 | 98 |

(8) Fluidizability

| Crystal Form | Karl Fluidity [R]* |
|---|---|
| $II_A$ | 21.3 |
| $II_B$ | 23.1 |
| $I_B$ | 18.2 |

$$*R = 39.017 + 78.485 \left( \frac{V_E}{V_\eta} \right) - 69.445 \sin \theta$$

$V_E$ = Apparent specific volume
$V_\eta$ = Tapped specific volume
$\theta$ = Angle of repose (9) Pelletizability The preparation of II type crystals will now be illustrated by the following non-limiting examples. These examples are offered only for purposes of illustration.

EXAMPLE 1

A crystalline sludge of AP obtained by separating into a solid and a liquid by a centrifugal separator was dried in an air flow drier for 2–3 seconds, then left in a constant temperature drier at 100° C. for 2 hours to obtain $II_B$ type AP crystal powder. 323 g of water was added to 600 g of the powder kneaded on a kneader for 15 minutes (moisture content of the kneaded product 35%), and said kneaded product was pelletized by extruding through a 2.0 m/m screen. This pelletized product was dried in a fluidized drier using a hot air at 85° C. to obtain a dried pelletized product of AP.

On the other hand, for comparison, 291 g of water was added to 600 g of $I_B$ type crystal powder, kneaded (moisture content of the kneaded product 35%) and similarly pelletized and dried.

The obtained results are shown in the following table.

| Crystal | Kneading Properties | Pelletizability | Drying | Coarse Specific Volume ml/g | Tapped Specific Volume ml/g | Dispersibility sec | Solubility sec |
|---|---|---|---|---|---|---|---|
| $II_B$ type | | | | | | | |
| (Starting Material) | 0 | 0 | 0 | 2.7 | 1.5 | 10–12 | 260 |
| (Pelletized Product) | | | | 2.6 | 2.2 | 4 | 26 |
| $I_B$ type | | | | | | | |
| (Starting Material) | | | | 4.1 | 2.1 | 2–4 | 140 |
| (Pelletized Product) | Crispy | Brittle | Granulated | | | | |

Coarse Specific Volume:

Measure by a bulk density meter according to JIS L 6721. The numeral value expresses the ratio of the volume to the weight of the content filled in a 100 cc cylindrical container.

Packed Specific Volume:

Measured after tapping 150 times using a tapping device for a powder tester (manufactured by Hosokawa Tekko Co.). The numeral has the same meaning as with the case of the coarse specific volume.

Dispersibility and Solubility:

0.05 g of AP was added to 150 ml of warm water at 60° C. with stirring, and the time until AP has been dispersed in water (dispersibility) and the time until completely dissolved (solubility) were measured.

As has been described above, in the case of $II_B$ type crystals, since granules of a uniform size was obtained, and their solubility was greatly improved over that of the starting material powder with less fly loss and better fluidizability, they had physical properties permitting easy handling, whereas, in the case of the $I_B$ type crystals, pelletization was difficult, and the pelletized product was broken on drying and turned into a fine powder.

EXAMPLE 2

A cylindrical sludge of AP obtained by separating into a solid and a liquid by a centrifugal separator was used and dried at a hot air temperature of 100° C. and an aerating speed of 1 m/sec. When the exhaust air temperature reached a constant value of 96° C., this was left for another 30 minutes to obtain $II_A$ type crystals, which were then pelletized similarly as in Example 1.

The obtained results are shown in the following table.

| Crystal | Kneading Properties | Pelletizability | Drying | Coarse Specific Volume cc/g | Tapped Specific Volume cc/g | Dispersibility sec | Solubility sec |
|---|---|---|---|---|---|---|---|
| $II_A$ type (Starting Material) | 0 | 0 | 0 | 2.9 | 1.6 | 8 | 170 |
| (Pelletized Product) | | | | 2.6 | 2.2 | 4 | 27 |

EXAMPLE 3

1.4 kg of water was added to 2.5 kg of $II_B$ type AP crystalline powder (moisture content of the mixture 35%), mixed and pelletized using a granulator (manufactured by Fuji Sangyo Co.) and the granulated product was dried by a fluidized drier similarly as in Example 1. On the other hand, as a control, 1.3 kg of water was added to 2.5 kg of $I_B$ type crystals (moisture content of the mixture 35%) and pelletized and dried in a similar manner.

| Crystal | Pelletizability | Coarse Specific volume ml/g | Fluidizability | Dispersibility sec | Solubility sec |
|---|---|---|---|---|---|
| $II_B$ type (Starting Material) | 0 | 2.7 | X | 10-12 | 260 |
| (Pelletized Product) | 0 | 3.0 | 0 | 1 | 50 |
| $I_B$ type (Starting Material) | Does not pelletize | 4.1 | X | 2-4 | 140 |
| (Pelletized Product) | | — | — | — | — |

The crystals of the present invention consist of two kinds, namely, $II_A$ type and $II_B$ type, but since they are very similar in structure and because they interconvert easily according to the humidity, it has been determined that these crystals belong to the same group and thus are referred to as II type crystals as a whole. These II type crystals, both $II_A$ type and $II_B$ type, are different from any of the conventional I type crystals, that is, $I_A$ type and $I_B$ type in the X-ray diffraction pattern and also in the equilibrium moisture content, and therefore they are novel crystals.

The II type crystals of the present invention may be obtained by drying I type crystals at about 80° C. or higher.

As for producing AP, various processes, including a synthesizing process, an enzymatic process etc. are known, and it may be noted that the crystals of the present invention may be obtained regardless of the process used to produce the AP. The I type crystals may be either $I_A$ type and $I_B$ type.

The drying temperature is about 80° C., and at 70° C., for example, II type crystals cannot be obtained. On the other hand, it is not desired to raise to 150° C. or higher in view of the decomposition of AP, and in particular, about 85°–120° C. is preferred. The drying time must be adequate to ensure that the crystals have converted to II type crystals. For example, in the case of 80° C., the drying time is generally about 6 hours, while in the case of 90° C., about an hour will suffice.

Crystals obtained by neutralizing, crystallizing, centrifugally separating and washing with water in a similar manner to that in Example 1 described hereinbelow were dried under reduced pressure at various temperatures, and the form of the dried crystals in relation to the drying temperature and time and also the amount of diketopiperadine contained therein were measured. The results are shown in the following table.

| Temperature | Time | | | |
|---|---|---|---|---|
| | 0.5 hr. | 1 hr. | 6 hrs. | Overnight |
| 60° C. | $I_B$ (Tr.) | $I_B$ (Tr.) | $I_B$ (Tr.) | $I_B$ (0.02%) |
| 70° C. | $I_B$ (Tr.) | $I_B$ (Tr.) | $I_B$ (Tr.) | $I_B$ (0.03%) |
| 80° C. | $I_B$ (Tr.) | $I_B$ (0.02%) | $II_A$ (0.05%) | $II_B$ (0.13%) |
| 90° C. | $I_B$ (0.001%) | $II_A$ (0.04%) | $II_B$ (0.12%) | $II_B$ (0.27%) |

-continued

| Temperature | Time | | | |
|---|---|---|---|---|
| | 0.5 hr. | 1 hr. | 6 hrs. | Overnight |
| 100° C. | II$_B$ (0.03%) | II$_B$ (0.07%) | II$_B$ (0.35%) | II$_B$ (0.81%) |

Content of diketopiperadine contained in crystals are in brackets.

While the drier may be a conventional one, a mode which permits a relatively long retention time, for example, a tray drier, an air dryer, a fluidized drier etc., is preferred.

A gas stream drier, such as a spray drier, a micron drier etc., is not suitable because the retention time is short, but if such a drier is to be employed, II type crystals may be obtained by connecting to a device for maintaining the drier powder at about 80° C. or higher, for example, a solid heater such as a torus disc type, a paddle heater type etc.

The thus obtained II type crystals may be made into a product per se or may further be pelletized. Even where pelletized, it is not necessary to add a binder such as a sizing agent etc. but II type crystals may be once changed into I type crystals by spraying about 25–45% of the crystals of water pelletized by e.g. an extrusion pelletizer, and redried. Although the redried product may be II type crystals, it is desired to change them into II type crystals in view of the moisture absorption characteristics. The important point in the pelletizing method is to utilize the caking properties manifested at the time of transition of II type crystals to I type crystals. It is presumed that such caking properties are brought about in the crystal transition process which involves recrystallization from a solution in such manner that minute twig-like crystals separate first on recrystallization and they become entangled to apparently increase the viscosity.

The crystals of the present invention have various advantages, for example, they are low in moisture absorption, stable when stored and easily pelletizable. Further, they are good in fluidizability and hence excellent in powder handling properties.

The following examples will illustrate the preparation of the II type crystals.

Producing The II Type Crystals

EXAMPLE 1

37 g of crystals of AP hydrochloride were dissolved in 500 ml of water at normal temperature, and neutralized to pH 5.0 with a 10% sodium carbonate solution to induce AP crystals to separate. These crystals were separated by a centrifugal separator, further washed with water, the obtained crystals were halved, and they were dried overnight, one half being in a reduced pressure drier controlled at 70° C. and the other half in a reduced pressure drier controlled at 90° C., to obtain 11.8 g of Crystal A (drier at 70° C.) and 11.2 g of Crystal B (dried at 90° C.). When the powder x-ray diffractions of these crystals were measured, Crystal A showed a crystal structure of I$_B$ type and Crystal B showed II$_B$ type.

EXAMPLE 2

43 g of N-carbobenzoxy-α-L-aspartyl-L-phenylalanine methyl ester was dissolved in 400 ml of methanol-water (1:1) and catalytically hydrogenated using 0.4 g of a 5% Pd-C catalyst under normal pressure and at 55° C. for 4 hours, the catalyst was filtered off, and then the reaction mixture was left in a refrigerator overnight to induce AP crystals to separate. These crystals was filtered out by a Buchner funnel and dried in a constant temperature drier controlled at 85° C. for 6 hours to obtain 23.4 g of crystals. When measured for a powder X-ray diffraction, these crystals showed a crystal form of II$_B$ type.

EXAMPLE 3

3.00 of I$_B$ type crystals of AP obtained in Example 1 were taken into a Petri dish, which was then stored in a constant temperature cell controlled at 80° C. overnight, and thereafter powder X-ray diffraction of the crystals was measured The crystals had been transformed into II$_B$ type.

EXAMPLE 4

500 g of AP was dissolved in 12 l of water of 60° C., and cooled to 50° C. with stirring to induce crystals to separate, after which the crystals were separated by a centrifugal separator, to obtain 677 g of wet crystals (water content 45.3%). 500 g of these wet crystals were placed in an aerating drier having an effective drying surface area of 0.08 m$^2$ and dried under conditions of a hot air temperature of 90° C. and a wind speed of 1.0 m/s for an hour. The exhaust air temperature at the end was 87° C., reaching more or less a constant temperature.

The obtained crystals were ground and measured for the powder X-ray diffraction, it showed II$_A$ crystals.

STORAGE STABLE TABLETS OR GRANULES OF AP

Many attempts have been made to date to formulate AP as a sweetener for commercial use. For example, a method of AP formulation is known whereby AP is granulated together with an excipient having high solubility. Another method is known whereby AP is formed into an effervescent tablet which effervesces on dissolution.

However, in such granulating or tabletting, another problem attributable to the excipient etc. used is brought about. In other words, since sugar, dextrin or the like is generally used as an excipient, an aminocarbonylation reaction proceeds between Aspartame and such an excipient during storage, often resulting in the deterioration in appearance due to browning, the loss of sweetness due to the decomposition of Aspartame etc. Further, during storage, a small amount of water incorporated or humidity in atmosphere tends to cause a reduction in fluidizability or solubility in the case of granules or a reduction in disintegration properties and dispersibility or solubility when added to water in the case of tablets. In particular, in the case of effervescent tablets, since a reaction between an effervescing agent (carbonate, bicarbonate etc.) and a neutralizing agent (acidic substance) starts during storage and hence the effervescence after storage is reduced, the solubility is remarkably deteriorated, and adhesion is brought about between the tablets per se or between the tablets and the container due to the moisture generated by the neutralization reaction or the moisture adsorbed.

The present inventors have thus discovered that by heating the conventional Aspartame I type crystals, i.e. I$_A$ type crystals or I$_B$ type crystals at 80° C. or higher, two novel kinds of crystals which interconvert from one to another can be obtained and these crystals have excellent physical properties and storage stability. The present inventors have also found that these crystals, i.e. Aspartame II type crystals are very stable even in the co-presence of the above-described excipient, effervescing agent, neutralizing agent etc. and further in the case of effervescent tablets, the progress of the neutralization reaction tends to be remarkably inhibited as compared with the conventional I type crystals.

The Aspartame II type crystals used in the present invention are two kinds of crystals, i.e. $II_A$ type crystals and $II_B$ type crystals, which are transformed to each other according to the humidity and when measured by a powder X-ray diffractometer using $CuK_\alpha$ radiation, the $II_A$ type crystals exhibit peaks of diffracted X-rays at angles of diffraction of at least 20.6°, 21.2°, 5.0° and 11.1° while the $II_B$ type crystals exhibit peaks of diffracted X-rays at angles of diffraction of at least 15.2°, 11.1°, 19.6° and 4.5°, and both crystals are crystals having an equilibrium moisture content of not higher than 3% at a temperature of 34° C. and a relative humidity of 78%, and, more specifically, they may be obtained by, for example, drying Aspartame I type crystals at about 80° C. or higher.

The physical property values of Aspartame II type crystals obtained in Production Examples 1-4 are shown below:

(1) X-ray Diffraction

An X-ray diffraction pattern of $II_A$ type crystals measured by a powder X-ray diffractometer using $CuK_\alpha$ radiation is shown in FIG. 1; an X-ray diffraction pattern of $II_B$ type crystals in FIG. 2; an X-ray diffraction pattern of the conventional $I_A$ type crystals in FIG. 3; and an X-ray diffraction pattern of $I_B$ type crystals in FIG. 4.

As is clear from the figures, the peaks appearing at angles of diffraction of 20.6°, 21.2°, 5.0° and 11.1° in $II_A$ type crystals and the peaks appearing at angles of diffraction of 15.2°, 11.1°, 19.6° and 4.5° in $II_B$ type crystals are found in neither conventional $I_A$ type crystals nor $I_B$ type crystals, and therefore $II_A$ type crystals and $II_B$ type crystals can be distinguished from I type crystals by these diffracted X-rays.

(2) Melting point $II_A$ type crystals 163° C. (dec.)
$II_B$ type crystals 171° C. (dec.)
$I_A$ type crystals 172° C. (dec.)

(3) Degree of Optical Rotation $II_A$ type crystals $[\alpha]_D^{20} = 15.9$
$II_B$ type crystals $[\alpha]_D^{20} = 16.1$
$I_B$ type crystals $[\alpha]_D^{20} = 16.0$ (4) Moisture Content It is about 0.9% to about 3% with $II_A$ type crystals and about 0.9% or less with $II_B$ type crystals, and within this range it changes continuously according to the humidity. On the other hand, it is about 6% or higher with $I_A$ type crystals and about 2% to about 6% with $I_B$ type crystals, and within this range it changed continuously according to the humidity. Wet crystals obtained by conventional crystallization are of a $I_A$ type.

The dipeptide sweetener-containing tablets or granules of the present invention utilize the above-described Aspartame II type crystals as the whole or a part of the sweetener. It is also possible to combine Aspartame II type crystals with other natural or artificial sweeteners, such as sugars, sugar alcohols, steviosides, or acesulfame K, for example, as additional sweeteners. Further, while it is also possible to use Aspartame I type crystals in addition, it is preferred to use Aspartame II type crystals singly.

The production of tablets or granules and other starting materials are not particularly restricted. In fact, they may follow the production process and starting material formulations described below.

As an excipient, one or more sugars other than Aspartame, such as sucrose, glucose, lactose, maltitol, sorbitol, dextrin, or cyclodextrin, for example, or inorganic substances such as calcium phosphate or calcium sulfate and the like may be employed.

As the binding agent in the case where granulated or molded into granules, cubes or the like using a binding agent, water, alcohol, an aqueous solution of sugar or an inorganic substance or the like is appropriately selected and used.

As the effervescing agent and neutralizing agent in the effervesent tablets, an effervescing agent such as sodium bicarbonate etc., and a neutralizing agent such as malic acid, citric acid, fumaric acid, tartaric acid etc. may be added by appropriately combing them.

In addition to the above components, it is possible to formulate leucine, isoleucine, L-vlaine, sugar esters, magnesium stearate etc. as a lubricant for tablets and an appropriate disintegrating agent taking into consideration the production of tablets, etc. or to formulate testing and flavoring components etc. other than sweeteners depending on the necessity.

The shape and size of the tablets or granules are also not restricted. The tablets as herein used also encompass cubes and like shapes.

The mode for the production of granules may be any of mixed graulation, press granulation, extruding granulation, fluidization granulation, tambling granulation, crushing granulation and the like.

The mode for the production of tablets may also be know one, and they may be produced by mixing the above-described tablet components and subjecting to a direct powder compression method, a dry granule compression method etc.

In the production of granules or tablets, Aspartame II type crystals obtained by the conversion from Aspartame I type crystals by previously drying at 80° C. or higher may be used as a starting material and granulated, or Aspartame I type crystals may be granulated or molded first and thereafter the granulated or molded product may be dried at about 80° C. or higher during the granulating or molding step. The drying temperature must be about 80° C. or higher. For example, if it is 70° C., the storage stability cannot be imparted. On the other hand, it is not desired to heat to 150° C. or higher in view of the decomposition of Aspartame, and about 80°-120° C. is particularly suitable. The drying time is until the transition to II type crystals is complete, and, for example, in the case of 80° C., about 6 hours may be satisfactory while in the case of 90° C., about an hour may suffice.

PRODUCTION EXAMPLE 1

37 g of crystals of Aspartame hydrochloride were dissolved in 500 ml of water at normal temperature, and neutralized to pH 5.0 with a 10% sodium carbonate solution to induce Aspartame crystals to separate. These crystals were separated by a centrifugal separator, further washed with water, the obtained crystals were halved, and they were dried overnight, one half being in a reduced pressure drier controlled at 70° C. and the other half in a reduced pressure drier controlled at 90° C., to obtain 11.8 g of Crystal A (dried at 70° C.) and 11.2 g of Crystal B (dried at 90° C.). When the powder X-ray diffractions of these crystals were measured, Crystal A showed a crystal structure of $I_B$ type and Crystal B showed $II_B$ type.

PRODUCTION EXAMPLE 2

43 g of N-carbobenzoxy-α-L-aspartyl-L-phenylalanine methyl ester was dissolved in 400 ml of methanol-water (1:1) and catalytically hydrogenated using 0.4 g of a 5% Pd-C catalyst under normal pressure and at 55° C. for 4 hours, the catalyst was filtered off, and then the reaction mixture was left in a refrigerator overight to induce Aspartame crystals to separate. These crystals were filtered out by a Buchner funnel and dried in a constant temperature drier controlled at 85° C. for 6 hours to obtain 23.4 g of crystals. By the powder X-ray diffraction, it was shown that crystal form of these crystals was $II_B$ type.

PRODUCTION EXAMPLE 3

3.00 g of $I_B$ type crystals of Aspartame obtained in Production Example 1 were taken into a Petri dish, which was then stored in a constant temperature cell controlled at 80° C. overnight, and thereafter powder X-ray diffraction of the crystals was measured. The crystals had been transformed to $II_B$ type.

PRODUCTION EXAMPLE 4

500 g of Aspartame was dissolved in 12 l of water of 60° C., and cooled to 50° C. with stirring to induce crystals to separate, after which the crystals were separated by a centrifugal separator, to obtain 677 g of wet crystals (water content 45.3%). 500 g of these wet crystals were placed in an aerating drier having an effective aerating drying surface area of 0.08 m² and dried under conditions of a hot air temperature of 90° C. and a wind speed of 1.0 m/s for an hour. The exhaust air temperature at the end was 87° C., reaching more or less a constant temperature.

The obtained crystals were ground and, when measured for the powder X-ray diffraction, it showed $II_A$ crystals.

EXAMPLE 1

Effervescent tablets having the composition shown in the following table were produced by a dry granule compression method.

TABLE 1

| Tablet Composition | | |
|---|---|---|
| | (% Compositional Proportion) | |
| Sample | Invention Section | Control Section |
| Aspartame II type crystals *1 | 22 | — |
| I type crystals *2 | — | 22 |
| β - Cyclodextrin *3 | 33 | 33 |
| Sodium bicarbonate | 24 | 24 |
| Citric acid | 20 | 20 |
| Sugar ester | 1 | 1 |

*1 $II_B$ Type crystals obtained by Production Example 1
*2 $I_B$ Type crystals obtained by Production Example 2
*3 Tradename: RINGDEX-B (produced by Sanraku Ocean Co.)

The respective samples were smooth in machine operations in both slug tabletting and main tabletting steps and showed good producing properties.

The thus obtained tablets were stored in open conditions (by placing 50 tablets in each weighing bottle and leaving it without a lid). Storage conditions were torturing conditions of 44° C. and RH 78%. The results are shown in Table 2.

TABLE 2

| Results of the Storing Test of Effervescent Tables | | | | |
|---|---|---|---|---|
| | | | Storing Period | |
| Sample | Measuring Item | Start | 1st Week | 2nd Week |
| Invention Section | Appearance *1 | O | O | O |
| | Solubility(sec) *2 | 17 | 18 | 18 |
| | Browning (b value) *3 | 2.08 | 4.36 | 5.62 |
| Control Section | Appearance *1 | O | O | Δ |
| | Solubility(sec) *2 | 18 | 20 | 23 |
| | Browning (b value) *3 | 1.28 | 5.01 | 7.21 |

*1 Roughness and cracking of the tablet surface as observed by the naked eyes: O Good, Δ Moderate, X Poor.
*2 Time from when added to 500 ml of warm water at 60° C. till completely dissolved.
*3 b Value as measured by a color difference meter; the higher the b value, the more yellow.

That is, as is clear from Table 2, the tablets according to the present invention showed almost no change in appearance or solubility due to storage and also the browning was small. As compared with these, in the case of the tablets in the control section using $I_A$ type crystals, since the reaction of the effervescing agent had proceeded due to moisture absorption and hence the disintegrating power at the time of dissolution was low, the solubility was reduced. Further, since the increase of the b value was extreme. Also in appearance, a soft and wet feel was imparted.

EXAMPLE 2

Non-effervescent tablets have the composition shown in the following table were produced by a dry granule compression method.

TABLE 3

| Tablet Compression | | |
|---|---|---|
| | (% Compositional Proportion) | |
| | Invention Section | Control Section |
| Aspartame II type crystals *1 | 22 | — |
| I type crystals *2 | — | 22 |
| Avicel *3 | 10 | 10 |
| β - Cyclodextrin | 62 | 62 |
| L-Valine | 6 | 6 |

*1 $II_B$ Type crystals obtained by Production Example 3
*2 $I_B$ Type crystals obtained by Production Example 4
*3 Crystalline cellulose produced by Ashai Chemical The respective samples were smooth in machine operations in both slug tabletting and main tabletting steps and showed good producing properties. The thus obtained tablets were subjected to a storing test in a manner similar to that of Example 1 to compare the storability. The results are shown in Table 4.

TABLE 4

| Results of the Storing Test of Disintegrating Tablets | | | | |
|---|---|---|---|---|
| | | | Storing Period | |
| Sample | Measuring Item | Start | 1st Week | 2nd Week |
| Invention Section | Moisture *1 | 2.7 | 6.5 | 11.7 |
| | Hardness (kg) *2 | 0.9 | 0.7 | 0.6 |
| | Appearance | 0 | 0 | |
| Control Section | Moisture (%) | 3.5 | 25.6 | 20.5 |
| | Hardness (kg) | 0.8 | 0.1 | 0 |

TABLE 4-continued

| Results of the Storing Test of Disintegrating Tablets | | | | |
|---|---|---|---|---|
| | | \multicolumn{3}{c}{Storing Period} | | |
| Sample | Measuring Item | Start | 1st Week | 2nd Week |
| | Appearance | 0 | x | |

*1 Drying loss method, 105° C., 4 hrs.
*2 Hardness at break as measured on a kiya-type hardmeter (5 kg)

That is, as is clear from Table 4, the tablets according to the present invention showed a smaller increase in moisture and also a less reduction in hardness as compared with the control section. With the control section, by storage of merely about a week, moisture absorption was extreme and the tablets were consolidated to one another. The appearance and shape of these did not keep the original condition of the tablets.

EXAMPLE 3

The Aspartame $II_A$ type crystals obtained in Production Example 4 were compression molded using a "roller compacter" (Model TF-MINI manufactured by Freunt Sangyo) under conditions of a screw of type X, a rotation of 15 rpm, a roll of type S, a rotation of 3 rpm and a pressure of 0.66–0.94 t/cm to obtain compressed flakes. These flakes were crused on a speed mill, and pelletized on a pelletizer ("oscillator" 16 mesh screen) to obtain Aspartame granules.

As a control, the Aspartame $I_B$ type crystals obtained in Production Example 1 were granulated into granules in a similar manner. The obtained granules were subjected to a storing test similarly as in the case of Example 1 and 2, to compare the storability. The results are shown in Table 5.

TABLE 5

| Results of the Storing Test of Aspartame Granules | | | |
|---|---|---|---|
| | \multicolumn{3}{c}{Change in Moisture with Time (%)} | | |
| Sample | Start | 5 hours | 24 hours |
| Invention Section | | | |
| ($II_B$ type crystalline granules) | 0.7 | 2.7 | 2.8 |
| Control Section | | | |
| ($I_B$ type crystalline granules) | 4.0 | 7.9 | 10.0 |

That is, the granules in the invention section using the Aspartame $II_B$ type crystals showed a smaller increase in moisture, having reached almost equilibrium at about 2.8%. On the other hand, the granules of the control section using the $I_B$ type crystals had a larger increase in moisture due to storage, and did not reached equilibrium even after 24 hours and was observed to still further absorb moisture.

EXAMPLE 4

Aspartame-containing granules were produced according to the formulation shown below and using a flow pelletizing method.

TABLE 6

| Formulation for Granules | | |
|---|---|---|
| | \multicolumn{2}{c}{(Unit: Parts by weight)} | |
| | Invention Section | Control Section |
| Aspartame $II_B$ type crystals | 5 | — |
| Aspartame $I_B$ type crystals | — | 5 |
| Amicohl 7H* | 95 | 95 |
| Water | 12 | 12 |

*Dextrin produced by Nichiden Kagaku

As a result, the granule strength (degree of powdering) of the obtained granules was measured to obtained the result shown in Table 7. That is, the granules of the present invention starting from the $II_B$ type crystals were evaluated as being higher in granule strength (smaller in degree of powdering) and better in product stability on distribution as compared with the control section.

TABLE 7

| Strength of Granules* | |
|---|---|
| Invention Section | Control Section |
| 2.2% | 6.5% |

*Granule Strength

80 Mesh-on granules are filled into a predetermined cylindrical container to 80% by volume at an oscillation of 4 cm for an hour. After shaking, they are sifted into 80 mesh on and pass using a sifter (for 10 minutes), and the degree of powdering is determined by the following equation:

$$\text{Degree of Powdering (\%)} = \frac{\text{80 Mesh Pass Product}}{\text{Total Amount}}$$

The degree of powdering as determined above is important as the smaller the degree of powdering, the greater the granule strength.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. α-L-aspartyl-L-phenylalanine methyl ester II crystals consisting of two kinds of crystals, $II_A$ and $II_B$, which interconvert from one to the other depending upon the equilibrium moisture content of the crystals, wherein one type of crystal, $II_A$, exhibits X-ray diffraction peaks at angles of diffraction of at least 20.6°, 21.2°, 5.0° and 11.1°, and the other type of crystal, $II_B$ type, exhibits X-ray diffraction peaks at angles of diffraction of at least 15.2°, 11.1°, 19.6°, 4.5°, as measured by X-ray diffractometer using $CuK_\alpha$ radiation and wherein the equilibrium moisture content of either of the crystals at a relative humidity of 78% is not higher than about 3% wherein said α-L-aspartyl-L-phenylalanine methyl ester II crystals are prepared by drying α-L-aspartyl-L-phenylalanine methyl ester I crystals at a temperature in the range of about 80° C. to less than 150° C. for a time sufficient to convert substantially all of the I crystals into the II crystals.

2. The $II_A$ and $II_B$ crystals according to claim 1, wherein said $II_A$ crystals have an equilibrium moisture content of about 0.9 to 3.0% and said $II_B$ crystals have an equilibrium moisture content of about 0.9% or less.

3. A process for the production of α-L-aspartyl-L-phenylalanine methyl ester II crystals, which comprises drying α-L-aspartyl-L-phenylalanine methyl ester I crystals at a temperature in the range of about 80° C. to less than 150° C. for a time sufficient to convert substantially all of the I crystals into the II crystals.

4. The process according to claim 3, wherein the crystals are dry crystals or wet crystals.

5. The process according to claim 3, wherein the crystals are dried with a tray dryer, air dryer or fluidized dryer.

6. The process according to claim 3, wherein the I crystals are dried with a gas stream dryer and the dried crystals are maintained at about 80° C. or higher so as to be converted into the II crystals.

* * * * *

UNITED STATES PATENT AND TRADEMARK OFFICE
CERTIFICATE OF CORRECTION

PATENT NO. : 4,579,747
DATED : April 1, 1986
INVENTOR(S) : Sugiyama Katsumi, et al It is certified that error appears in the above-identified patent and that said Letters Patent is hereby corrected as shown below:

On the title page:

-- The Priority Information has been omitted from the Letters Patent. It should read as follows:

44447/1983     JAPAN     March 18, 1983

The title on the Letters Patent is incorrect. It should read as follows:

Dipeptide Crystals and Process for their Preparation.

not

Dipeptide Crystals and Process for their Production. --

Signed and Sealed this

First Day of July 1986

[SEAL]

Attest:

DONALD J. QUIGG

Attesting Officer    Commissioner of Patents and Trademarks